(12) United States Patent
Chinn et al.

(10) Patent No.: US 6,685,442 B2
(45) Date of Patent: Feb. 3, 2004

(54) ACTUATOR DEVICE UTILIZING A CONDUCTIVE POLYMER GEL

(75) Inventors: Douglas A. Chinn, Livermore, CA (US); David J. Irvin, Ridgecrest, CA (US)

(73) Assignee: Sandia National Laboratories, Livermore, CA (US)

( * ) Notice: Subject to any disclaimer, the term of this patent is extended or adjusted under 35 U.S.C. 154(b) by 46 days.

(21) Appl. No.: 10/081,286

(22) Filed: Feb. 20, 2002

(65) Prior Publication Data

US 2003/0156953 A1 Aug. 21, 2003

(51) Int. Cl.$^7$ ............................ F04B 35/00; F04B 17/00
(52) U.S. Cl. ................... 417/321; 417/413.1; 417/322; 251/129.06
(58) Field of Search ................................ 417/321, 322, 417/413.1; 251/129.06

(56) References Cited

U.S. PATENT DOCUMENTS

| | | | | |
|---|---|---|---|---|
| 4,545,561 A | * | 10/1985 | Brown | 251/129.08 |
| 5,977,685 A | | 11/1999 | Kurita et al. | 310/311 |
| 6,030,442 A | | 2/2000 | Kabra et al. | 106/162.8 |
| 6,120,004 A | * | 9/2000 | Park et al. | 251/129.06 |
| 6,210,128 B1 | * | 4/2001 | Rife et al. | 417/322 |

OTHER PUBLICATIONS

Murthy, N. S.; Shacklette, L. W.; Baughmann, R. H.; "Effects of charge transfer on chain dimension in trans–polyacetylene" *J. Chem. Phys.* 1987, v. 87, (4), pp. 2346–2348.

Yoshino, K.; Nakao, K.; Morita, S.; Onoda, M.; "Doped Conducting Polymer Gel and its Characteristics as Functions of Solvent, Temperature and Electrochemical Doping Potential" *Jpn. J. Appl. Phys.* 1989, v. 28, (11) pp. L2027–L2030.

Winokur, M.; Walmsley, P.; Smith, J.; Heeger, A. J.; "Structural Evolution in Iodine–Doped Poly(3–alkylthiophenes)" *Macromolecules* 1991, v. 24, pp. 3812–3815.

Yoshino, K.; Morita, S.; Nakao, K.; "Characteristics of Conducting Polymer Gels and Their Doping Effects" *Synth. Met.* 1991, v. 41, pp. 1039–1044.

Otero, T. F.; Angulo, E.; Rodriguez, J.; Santamaria, C.; "Electrochemomechanical properties from a bilayer: polypyrrole/non–conducting and flexible materials—artificial muscle" *J. Electroanal. Chem.* 1992, v. 341, pp. 369–375.

Pei, Q.; Inganäs, O.; "Conjugated Ploymers and the Bending Canilever Method: Electrical Muscles and Smart Devices" *Adv. Mater.* 1992, v. 4, pp. 277–278.

Smela, E.; Inganäs, O.; Pei, Q.; Lundström, I.; "Electrochemical Muscles: Micromachining Fingers and Corkscrews" *Adv. Mater.* 1993, v. 5, pp. 630–632.

Pei, Q.; Inganäs, O.; "Electrochemical Applications of the Bending Beam Method. 2. Electroshrinking and Slow Relaxation in Polypyrrole" *J. Phys. Chem.* 1993, v. 97, pp. 6034–6041.

(List continued on next page.)

*Primary Examiner*—Charles G. Freay
(74) *Attorney, Agent, or Firm*—Timothy P. Evans

(57) ABSTRACT

A valve actuator based on a conductive polymer gel is disclosed. A nonconductive housing is provided having two separate chambers separated by a porous frit. The conductive polymer is held in one chamber and an electrolyte solution, used as a source of charged ions, is held in the second chamber. The ends of the housing a sealed with a flexible elastomer. The polymer gel is further provide with electrodes with which to apply an electrical potential across the gel in order to initiate an oxidation reaction which in turn drives anions across the porous frit and into the polymer gel, swelling the volume of the gel and simultaneously contracting the volume of the electrolyte solution. Because the two end chambers are sealed the flexible elastomer expands or contracts with the chamber volume change. By manipulating the potential across the gel the motion of the elastomer can be controlled to act as a "gate" to open or close a fluid channel and thereby control flow through that channel.

18 Claims, 7 Drawing Sheets

OTHER PUBLICATIONS

Pei, Q.; Inganäs, O.; "Electroelastomers: Conjugated Poly(3–Octylthiophene) Gels With Controlled Crosslinking" *Synth. Met.* 1993, v. 55–57, pp. 3724–3729.

Chiarelli, P.; Derossi, D.; Della Santa, A.; Mazzoldi A.; "Doping Induced Volume Changes in a π–congugated Conducting Polymer" *Polymer Gels and Networks* 1994, v. 2, pp. 289–297.

Smela, E.; Inganäs, O.; Lundström, I.;"Controlled Folding of Micrometer–Sized Structures" *Science* 1995, v. 268, pp. 1735–1738.

Chen, X.; Inganas, O.; "Doping–induced volume changes in poly(3–octylthiophene) solids and gels" *Synth. Met.* 1995, v. 74, pp. 159–164.

Gandhi, M. R.; Murray, P.; Spinks, G. M.; Wallace, G. G.; "Mechanism of electromechanical actuation in polypyrrole" *Synthetic Metals* 1995, v. 73, pp. 247–256.

Goll, C.; Bacher, W.; Bustgens B.; Maas, D.; Menz, W.; Schomburg, W.; "Microvalves with bistable buckled polymer diaphragms" *J. Micromech. Microeng.* 1996, v. 6, pp. 77–79.

Chen, X.; Ke–Zhao Xing, K. Z.; Inganäs O.; "Electrochemically Induced Volume Changes in Poly(3,4–ethylenedioxythionphene)" *Chem. Mater.* 1996, v. 8, pp. 2439–2443.

Lewis, T. W.; Moulton, S. E.; Spinks, G. M.; Wallace, G. G.; "Optimisation of a polypyrrole based actuator" *Synthetic Metals* 1997, v. 85, pp. 1419–1420.

Viallat, A.; Pepindonat, B.; "State of Gellation of Fully Conjugated Conducting Gels. Gel Fraction, Swelling, and Nuclear Magnetic Relaxation" *Macromolecules* 1997, v. 30, pp. 4679–4687.

Rasmussen, S. C.; Pickens, J. C.; Hutchison, J. E.; "A General Synthetic Route to 4–Substituted–2, 2'–Bithiophenes" *J. Heterocyclic Chem.* 1997, v. 34, 285–288.

Della Santa, A.; Mazzoldi, A.; Tonci, C.; Derossi, D.; "Passive mechanical properties of polypyrrole films: a continuum poroelastic model" *Materials Science&Engineering C* 1997, v. 5, pp. 101–109.

Li, J.; Aoki, K.; "Electrochemical gelation of poly(3–hexylthiophene) film" *J. Electroanal. Chem.* 1998, v. 453, pp. 107–112.

Kaneko, M.; Kaneto, K.; "Electrochemomechanical deformation in polyaniline and poly(o–methoxyaniline)" *Synth. Met.* 1999, 102, pp. 1350–1353.

Otero, T. F.; Bengoechea, M.; "UV–Visible Spectroelectrochemistry of Conducting Polymers. Energy Linked to Conformational Changes" *Langmuir* 1999, v. 15, pp. 1323–1327.

Madden, J. D.; Cush, R. A.; Kanigan, T. S.; Brenan, C. j.; Hunter, I. W.; "Encapsulated polypyrrole actuators" *Synth. Met.* 1999, v. 105, pp. 61–64.

Mangold, K–M.; Morgenschweis, K. Jüttner, K.; "Relaxation of polythiophenes bridged by alkyl chains" *Electrochimica Acta* 1999, v. 44, pp. 1865–1869.

Chen, L.; Kim, B.; Nishino, M.; Gong, J. P.; Osada, Y.; "Environmental Responses of Polythiophene Hydrogels" *Macromolecules* 2000, v. 33, pp. 1232–1236.

Goods, S.H.; Whinnery, L.L.; Irvin, D.J.; Korellis, J.S.; "Direct Measurement of Extension and Force in Conductive Polymer Gel Actuators," Sandia Report No. SAND2001–8199; 02/01 (Cataloged Mar. 26, 2001) 18 pp.

* cited by examiner

ACTUATOR DEVICE UTILIZING A CONDUCTIVE POLYMER GEL

The United States Government has rights in this invention pursuant to Contract No. DE-AC04-94AL85000 between the United States Department of Energy and Sandia Corporation for the operation of Sandia National Laboratories.

BACKGROUND OF THE INVENTION

1. Field of the Invention

The present invention relates to a conductive polymer gel and its application for driving a miniature actuator. In particular the present invention is drawn to a polythiophene-based conductive polymer gel used to open and close an actuator valve.

2. Background and Related Art

Current trends in the designs of analytical instrumentation, especially where fluids are used to carry analytes to various instrument stations for processing (such as separation, mixing, species detection, and the like), are increasingly tending toward integrated and miniaturized systems. However, it is generally recognized that these designs will only be possible with the development of fast and efficient micro-actuators that can be operated as pumps and valves. As analytical equipment is scaled down the mechanical structures comprising these devices must also decrease in size. As is often the case, however, such macroscopic designs are not easily scaled down and replicated as microdevices and still providing acceptable function. Thus there is a need for development of microscopic "machines" having useful performance characteristics. In this regard conductive polymers lend themselves well to such designs.

The basic premise of the present invention is to use a conductive polymer gel having the property of changing dimension upon application of a small electrical potential, typically less than 1 volt, as a value in an actuator. The expansion and contraction of a body comprising the polymer gel results from a potential induced change in the oxidation state of the polymer and the associated diffusion of charge balancing ions and their coordinating solvent into and out of the gel (FIG. 1). As the polymer is oxidized, it forms positive charges that reside on the "backbone" of the polymer chain. As solvent coordinated anions diffuse into the polymer to balance the charge, the dimensions of the sample increase as the result of osmotic pressure developed during the influx of the two species, and result in an effect that can be harnessed to produce useful work.

While a large body of prior art exists describing electrochemically driven swelling/de-swelling of conductive polymers none of the work in the literature has reported the direct measurement of the mechanical response of these materials to electrochemical stimulation. Neither is there any mention of the use of the work-producing effect of the response of these polymer gels to the application of small electrical potentials. Presumably, therefore, none have recognized the potential use of these materials as control members in micro-actuators.

Beginning in the late 1980's with Murthy, et al., (J. Chem. Phys. (1987), v. 87, pp. 2346) and more recently with Li and Aoki, (J. Electroanal. Chem. (1998), v. 453, pp. 107; Kaneko and Kaneto, (Synth. Met. (1999), v. 102, pp. 1350); Madden, et al., (Synth. Met. (1999), v. 105, pp. 61); and Otero and Bengoechea, (Langmuir (1999), v. 15, pp. 1323), a large body of work developed that described electrochemically driven swelling/de-swelling of conductive polymers. Our interest in these materials stems from their potential use as small-scale actuators, valves or pumps in microsystems applications. A much smaller body of art has reported measurements of the tensile forces (see, for instance, Chen, et al., Macromolecules (2000), v. 33, 1232) and shear modulus generated in pre-loaded thin films (Chen and Inganäs, Synth. Met. (1995) v. 74, 159).

SUMMARY OF THE INVENTION

In the present invention, the free extension, or closure forces (pressures), generated by these materials when they are confined, is characterized in an unambiguous manner. This work describes the synthesis of a polythiophene-based conductive polymer gel actuators. Measurements of gel extension and force in one axis under an applied square wave electrical stimulating pulse is shown.

It is therefore an object of this invention to provide a conductive polymer gel responsive to low electrical potentials.

It is another object of the invention to provide an actuator comprising said conductive polymer gel.

Yet another object of this invention is to provide a polythiophene polymer gel which is responsive to electrical potentials of less than ±1 volt.

Still another object of the invention is to provide a polymer gel actuator generating an axial pressure of about 2 pounds-force per square-inch under the influence of a +0.8 volt potential.

DETAILED DESCRIPTION OF THE INVENTION

Figure 1:
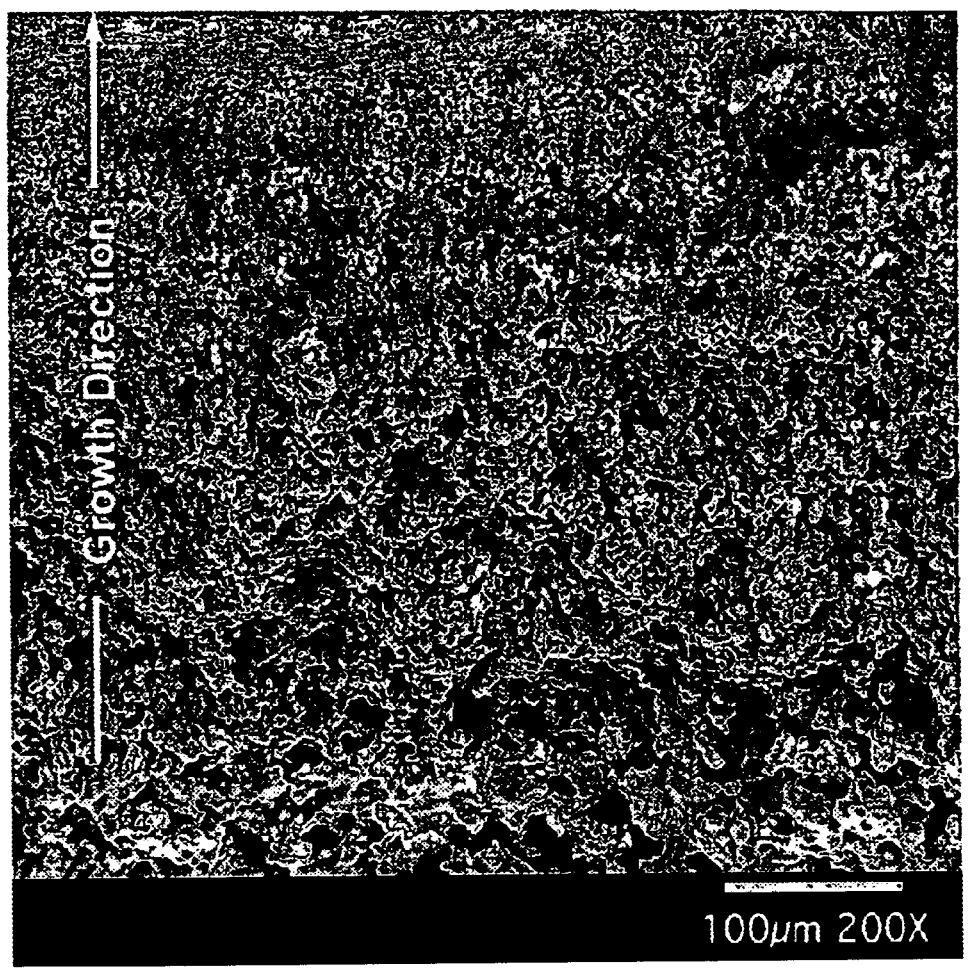
FIG. 1 shows a general depiction of the morphology of the fracture surface of a frozen layer of the polymer gel of the present invention.

Interest in conductive polymer gels stems from their potential use as small-scale actuators, valves or pumps in microsystems applications. Synthesis of the gels was performed by the process below and has been generally described by others although the synthesis of the cross-linking agent has not been generally described.

Synthesis of the Gel:

The gels of the present invention were prepared as described in a process developed by Pei and Inganäs, (see *Synth. Met* (1993), v. 55–57, pp. 3724–3729). Ferric chloride powder, at a concentration of 2.3 equivalents, was placed in a reaction vessel and cold chloroform was slowly added in order to minimize disruption of the $FeCl_3$. The vessel was then chilled to −30° C. After 2 hours, a solution of 3-octylthiophene ("OT"), 1,6-bis(2-thienyl)hexane (hereinafter "BTH"), and $CHCl_3$ was added and the vessel was placed in a refrigerator (4–5° C.) for 4 days. The supernant was then decanted from the resulting polymer mass. Methanol was added to the vessel to contract the chloroform-swollen gels. The polymer mass was then removed from the mold, placed in a Soxhlet® thimble and extracted with hot methanol for 24 hours. The resulting material contained less than 0.4% iron as determined by elemental analysis and inductively coupled plasma mass spectroscopy (ICP-MS). The measurement is an indication of the effectiveness of this purification method (It is believed that the purity of the gel is important to ensure its long term chemical and mechanical stability.). It is also important to note that only methanol, a mild reducing agent, was necessary.

Synthesis of the Cross-Linking Agent BTH:

While the synthesis of the polythiophene-based polymer gels has been published, the supporting references (Chen and Inganäs, *Synth. Met.* (1995) v. 74, pp. 159; Mangold, et al., *Electrochimica Acta* (1999), v. 44, pp. 1865) give only a general description of the synthesis of the cross-linking agent BTH (1,6-bis(2-thienyl)hexane). BTH was synthesized using a Ni-catalyst to cross-couple 3-bromothiophene and 1,6-diiodohexane in a technique described by Rasmussen, et al., (*J. Heterocyclic Chem.* (1997), v. 34, pp. 285). 1,6-diiodohexane was dissolved in ether containing 2.1 equivalents of magnesium turnings under an argon purge. Two-tenths (0.2) equivalent of 1,2-dibromoethane in ether was added slowly to allow control of the ether reflux. When the spontaneous reflux subsided, the reaction mixture was heated at reflux for 1 hour. The reaction mixture was then cooled with an ice bath and slowly transferred with the use of a polytetrafluoroethylene (PTFE) cannula to a chilled flask containing 3 equivalents of 3-bromothiophene, and 0.09 equivalents of [1,3-bis(diphenylphosphino)propane]-dichloro-nickel (II) (i.e., $Ni(dppp)Cl_2$) in ether, such that the temperature did not rise above 5° C. After the transfer was completed, the reaction was stirred at room temperature for 24 hours. The mixture was poured into a ten-fold excess of ice/1M HCl. The organic layer was washed with 1M HCl and water and dried over anhydrous $NaHCO_3$. The mixture was filtered, and the ether was removed by reduced pressure distillation. The remaining red oil was quickly distilled under vacuum to yield three fractions. The samples were refrigerated over 48 hours to yielding white crystals in two of the three fractions. The solid was collected by suction filtration and recrystallized to yield BTH. The structure was verified by $^1H$ and $^{13}C$ NMR and GCMS.

The samples synthesized by this method were found to have varying morphology as shown in a freeze-fracture sample seen in FIG. 1. The bottom of the as-cast material, where gel deposition initiates, has a large aggregate structure and fewer pores; the top has a very fine structure with much smaller pores. The density of solid polythiophene is about 1 $g/cm^3$. The measured bulk density of these gels is ~0.3 $g/cm^3$ indicating that they have a large free volume. This free volume is important because it will determine, in part, the rate at which solvent and ions will be able to flow into the gel.

Measurement of the Gel Displacement Behavior:

The load and displacement characteristics of this polymer gel have been characterized. Specimens for these measurements consisted of right cylinders cut from a larger sheet of the gel. These cylinders were nominally 3 mm in diameter and 2 mm tall. For each test, a cylinder was inserted into a porous polypropylene frit that had a machined bore slightly larger than the diameter of the specimen. The frit constrained the sides and bottom of the polymer sample while allowing for the influx of solvent and ion. A variety of working electrode geometries have been used. Most typically, a thin platinum wire (0.33 mm in diameter) was inserted into the bottom of the specimen along its cylindrical axis. Alternatively, a fine, wire mesh basket formed to surround the specimen, yields equivalent response. The frit/specimen assembly was then placed in the custom electrochemical cell consisting of a glass cylinder and a PTFE (polytetrafluoroethylene) spacer that was used to locate the polypropylene frit in a fixed position at the bottom of the cylinder. The spacer also had milled slots to locate the reference and counter electrodes. The testing apparatus allowed for either the measurement of the free displacement of the gel (that is, the unconstrained axial extension) or the measurement of force generation when the gel was fully constrained. The entire electrochemical cell assembly was then placed in an argon-purged boxed for testing. The samples were subjected to a square wave function with an oxidation pulse of +0.8 V vs. an $Ag/Ag^+$ standard electrode for one, five, or ten minutes, and a subsequent reduction pulse of −0.5V vs. the $Ag/Ag^+$ standard electrode for the same time resulting in a two, ten, or twenty minute period.

Figure 2:
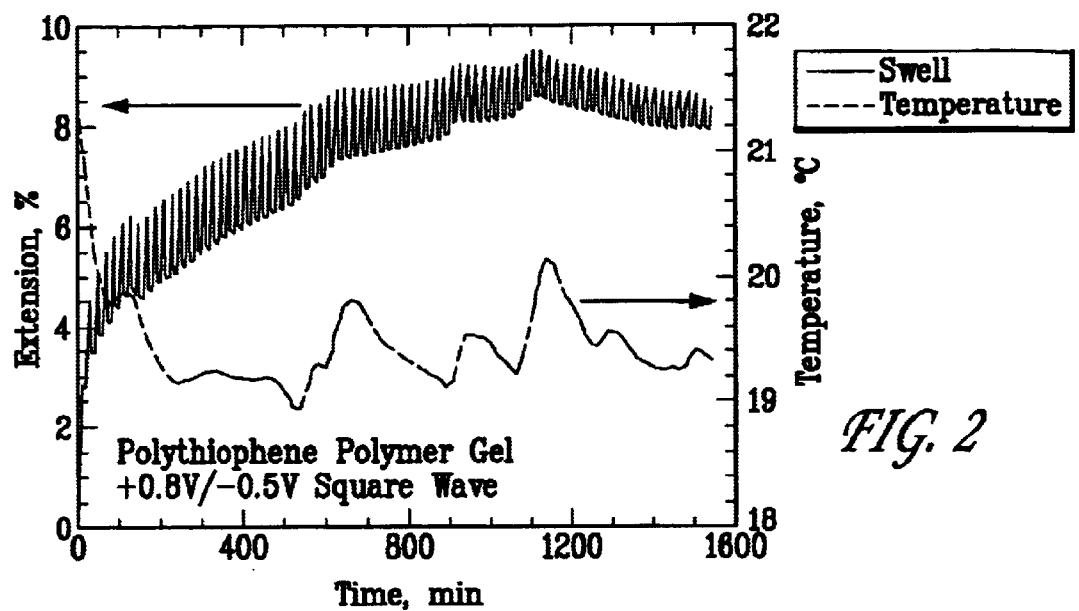
FIG. 2 illustrates the swell response of the polythiophene gel of this invention as a function of time for a 20 minute period, under the influence of a +0.8/−0.5V applied square wave potential.
Figure 4:
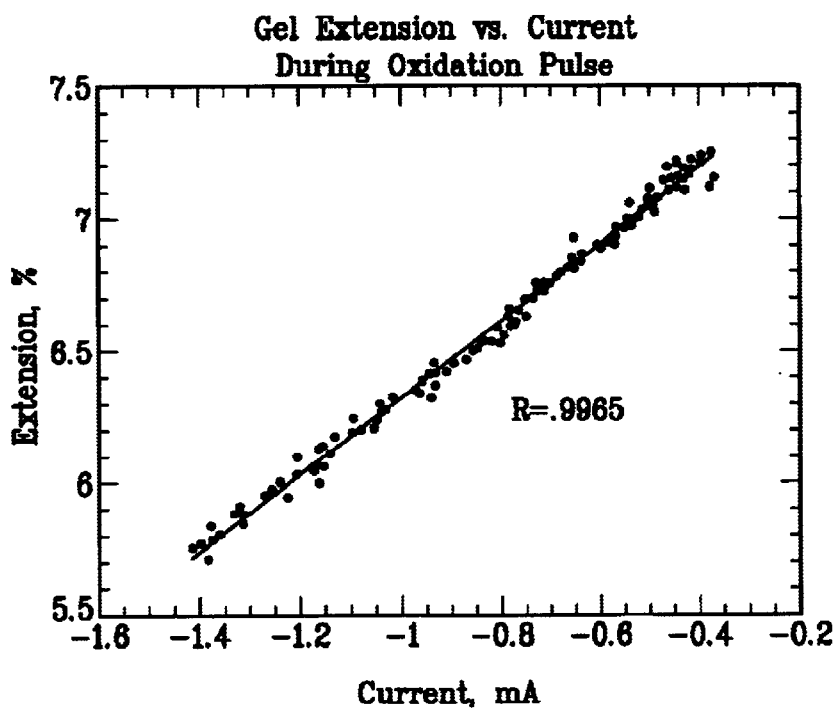
FIG. 4 illustrates the relationship between gel extension and cell current for one oxidation pulse at approximately 300 minutes into the test shown in FIG. 2.
Figure 3A:
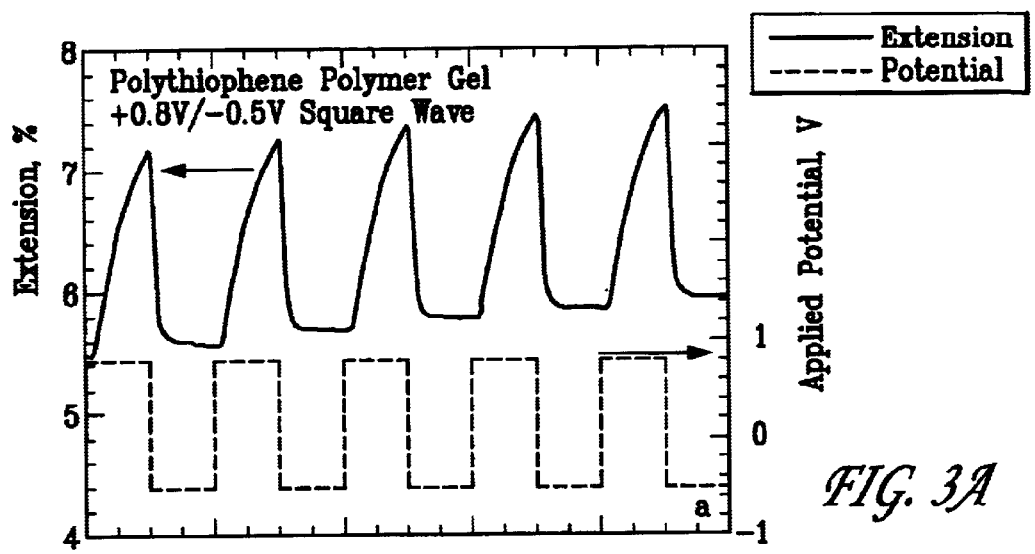
FIG. 3A shows a detailed view of the gel expansion and cell current vs. time for a portion of the test shown in FIG. 2.
Figure 3B:
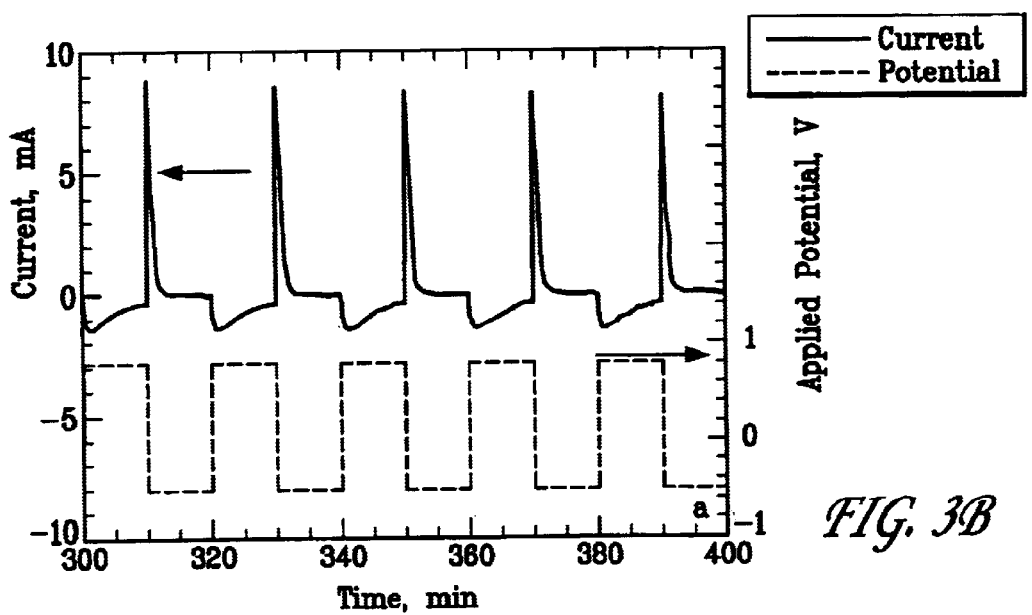
FIG. 3B shows the applied potential waveform for the results shown in FIGS. 2 and 3A.

The extension of the gel along the cylindrical axis was measured using a precision linear displacement transducer manufactured by Microstrain Inc. (Burlington, Vt.). Displacement in axial dimension was normalized to the initial height of the gel cylinder and the absolute change in height is reported as "Extension (%)". FIG. 2 shows the typical extension vs. time behavior over a long period of time for a gel specimen driven under a +0.8/−0.5 V square wave function having a 20 minute period. Over each cycle (i.e., one oxidation pulse followed by one reduction pulse, the axial change in dimension is approximately 1.5%. The extension is not fully recovered at the end of each reduction pulse and therefore there is a net increase in the axial length of the specimen over the >24 hours of total testing. The discontinuities in the evolution of the specimen length correspond to minor variations in the ambient temperature. It is believed that this effect is mostly an artifact resulting from thermal expansion and contraction of the test apparatus. The local temperature trace is also shown in FIG. 2. FIGS. 3A and 3B shows a portion of this test beginning at 300 minutes and continuing to 400 minutes, in greater detail. FIG. 3A shows both the axial extension as well as the applied voltage waveform. It is clear from this figure that, within each oxidation pulse, the axial extension is not linear with time. Rather, it falls monotonically with increasing pulse time. It can also be seen that the extension of the specimen does not commence instantaneously upon the onset of the oxidation pulse. Instead, there is an approximately 90 second lag time before the specimen begins to swell axially. FIG. 3B shows the current generated in the cell over the same time period. The current waveform is quite reproducible, peaking at ≈+8 mA at the onset of the reduction pulse and gradually approaching a minimum value of ≈−2 mA early in the oxidation pulse. Note should be taken that, unlike the extension, the current switches instantaneously with the applied voltage waveform. FIG. 4 shows the relationship between the change in the axial gel dimension and current flow in the cell during one arbitrary oxidation pulse. The trace represents a linear best fit through the data. Since the current is a measure of electron flow (and therefore counter ion flow in the cell) it is clear that there is a direct relationship between ion flow, uptake into the specimen and the resulting dimensional change of the gel.

Figure 5:
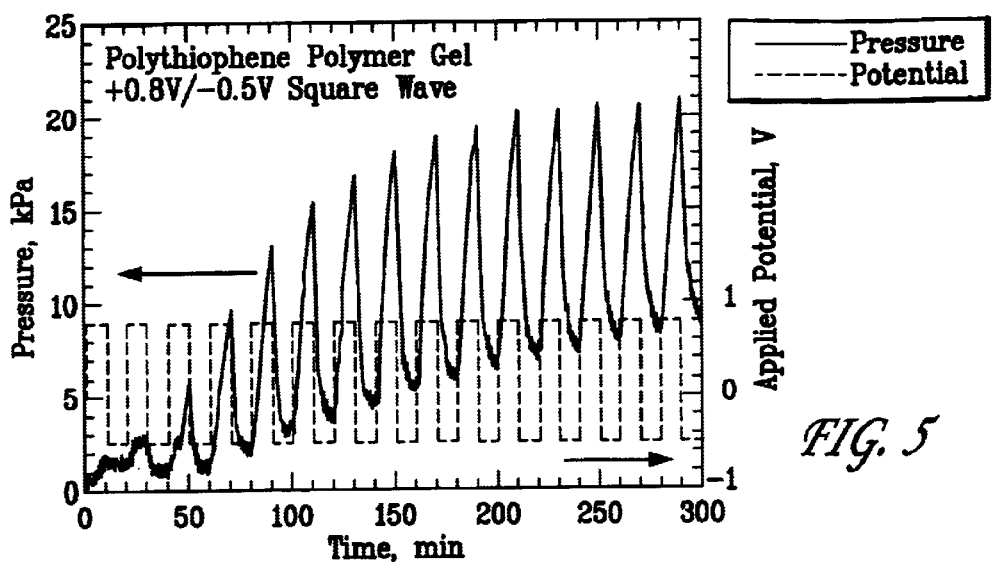
FIG. 5 illustrates the axial pressure generated by the polythiophene gel as a function of time for a 20 minute period under the influence of a +0.8/−0.5V applied square wave potential.

Lastly, the axial pressure generated by the expansion of the gel against a fixed surface was directly measured using a precision force transducer provided by Sensotec, Inc., (Columbus, Ohio); results are shown in FIG. 5. Such a measurement is equivalent to the closure pressures that would be generated if the gel were used as a valve to seal an orifice. Given the large free volume of the gel, the pressure generation is surprisingly high, especially given a specimen mass of only about 6 mg. The measured force is about 14 kPa (about 0.15 $kg_f/cm^2$ or about 2 psi) at steady state.

While the force generated in the first few cycles is minimal, as the gel expands to completely contact the transducer probe, after about three cycles the generation of a mean pressure pulse reflects the hysteresis in the expansion/contraction behavior illustrated in FIGS. 2, 3A and 3B.

Preferred Embodiments and Best Mode

Figure 6A:
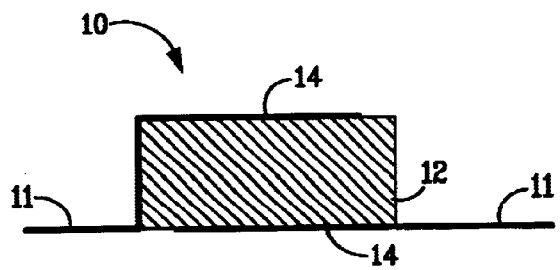
FIG. 6A illustrates the conductive gel plug assembled together with top and bottom porous electrodes.
Figure 6B:
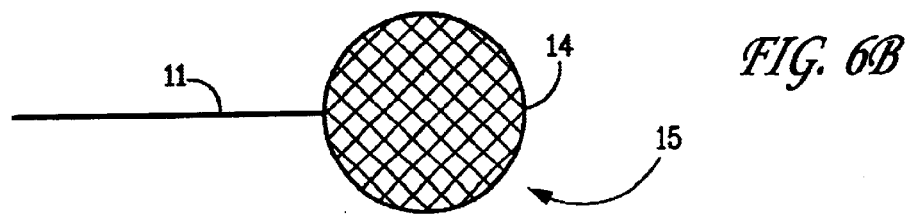
FIG. 6B illustrates one of porous electrodes and attached lead wire.
Figure 7:
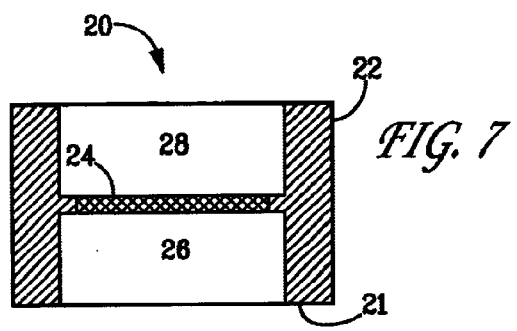
FIG. 7 illustrates the rigid, nonconductive housing with the porous membrane between the two interior recessed portions provided to hold the gel plug assembly and the electrolyte solution.

The gel of the present invention finds utility as a seal or diaphragm to regulate or control flow through miniature actuator assemblies. In one embodiment, illustrated in FIGS. 6–10, a small cylindrical plug 12 of the gel is formed in a mold or cut from a sheet of the polymer. Electrodes 15, formed by attaching a disk of a conductive porous mesh 14 to an electrode wire 11, as shown in FIG. 6B, are attached at top and bottom surfaces of plug 12, as shown in FIG. 6A, to form plug assembly 10. Alternatively, disk 14 may be a thin metal layer deposited directly onto a portion of the surface of gel plug 12, either by vapor, chemical or particle deposition, or low temperature sputtering.

Once formed, plug assembly 10 is immersed in an electrolyte solution, comprising charge balancing ions and an associated coordinated solvent species molecule. Although other solvent/salt systems are possible, the particular electrolyte system used in the present invention comprised a quaternary salt dissolved in an aprotic solvent, specifically 0.1M tetra-n-butyl ammonium perchlorate (CAS #1923-70-2) dissolved in acetonitrile. An electrical potential is then applied across electrode 15 until the polymer plug is stabilized and fully doped with solvent coordinated anions. The doped plug is then pressed into one side of a ring-shaped structure, or housing 20, having top and bottom chambers 26 and 28, seen in FIG. 7. Housing 20 has a porous member 24 situated between chambers 26 and 28 that separates and isolates each side of the housing but which allows for the passage of charged ion species with little or no interference. Housing 20 may be fabricated from materials such as polytetrafluoroethylenes, crystalline homopolymer acetal resins, polysulfones, polyurethanes, polyimides, polycarbonates, polymethylmethacrylates and similar polymers, moldable or machinable glasses, ceramics, silicon wafers and any other material that is, or can be, rendered nonconductive, rigid, and chemically inert. Porous member 24 may be a glass frit, a porous polymer, such as for example polypropylene, or a porous non-corroding metal, such as for example nickel.

Figure 8:
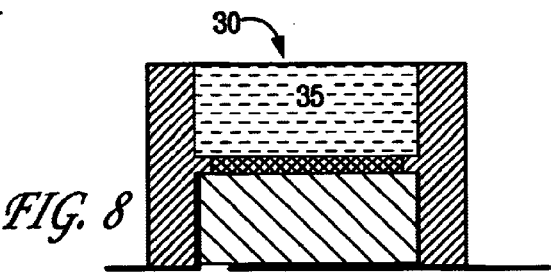
FIG. 8 illustrates the nonconductive housing into which the gel plug assembly and the electrolyte solution have been placed.

After inserting plug assembly 10, the opposite chamber of housing 20 is filled with a small quantity of electrolyte solution 35 (again 0.1M tetra-n-butyl ammonium perchlorate dissolved in acetonitrile) to form housing assembly 30, as shown in FIG. 8, which then can be sealed or encapsulated to provide actuator assembly 40.

Figure 9A:
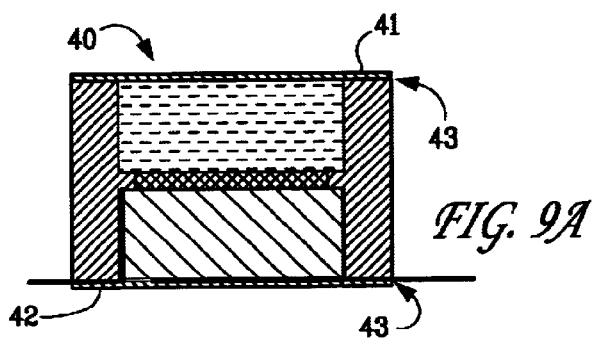
FIG. 9A illustrates the assembled housing covered by top and bottom flexible layers to provide the actuator assembly and FIG. 9B shows the assembled housing entirely sealed or encapsulated by a thin flexible coating to provide the actuator assembly.
Figure 9B:
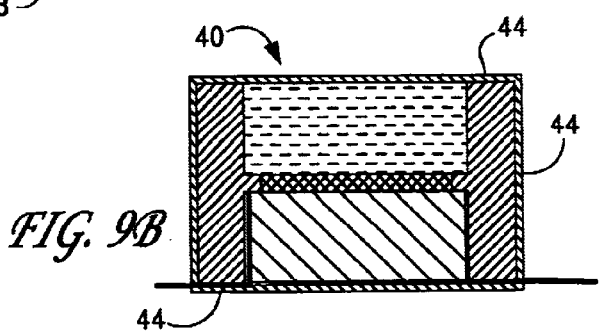

As shown in FIG. 9A housing assembly 30 is closed by gluing or otherwise bonding overlaying disks 41 and 42 of an elastomeric membrane such as a polyimide, a silicon-based elastomer, or some other flexible membrane, onto the end surfaces 11 of the housing. An adhesive 43 such a cyanoacrylates, cyanosilicones, cyanosiloxanes, polyurethanes, epoxies, and epoxy-polyamides, may be used to bond disks 41 and 42 to housing 10 (the choice of materials used to fabricate the housing, however, may also require a surface preparation process in order to achieve proper adhesion). Alternatively, as shown in FIG. 9B, housing assembly 30 is closed by completely encapsulating it with a thin, flexible conformal coating 44 of an inert elastomer such Silicoat®, or with a thin layer of a silicone adhesive, such as room temperature-vulcanizing polydimethylsiloxane, to provide actuator assembly 40. In either case, however, it is important that the ends of housing 20 are tightly sealed in order to prevent leakage of the electrolyte.

Figure 10A:
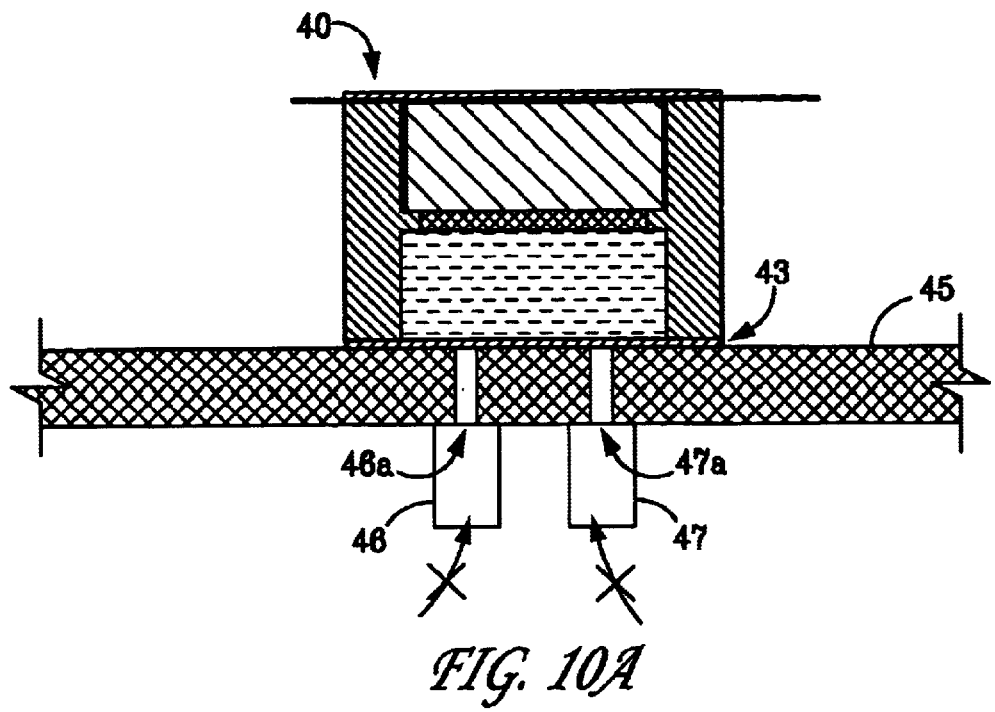
FIG. 10A illustrates the actuator assembly mounted onto a plenum in a first relationship so as to cover one or more fluid channels.
Figure 10B:
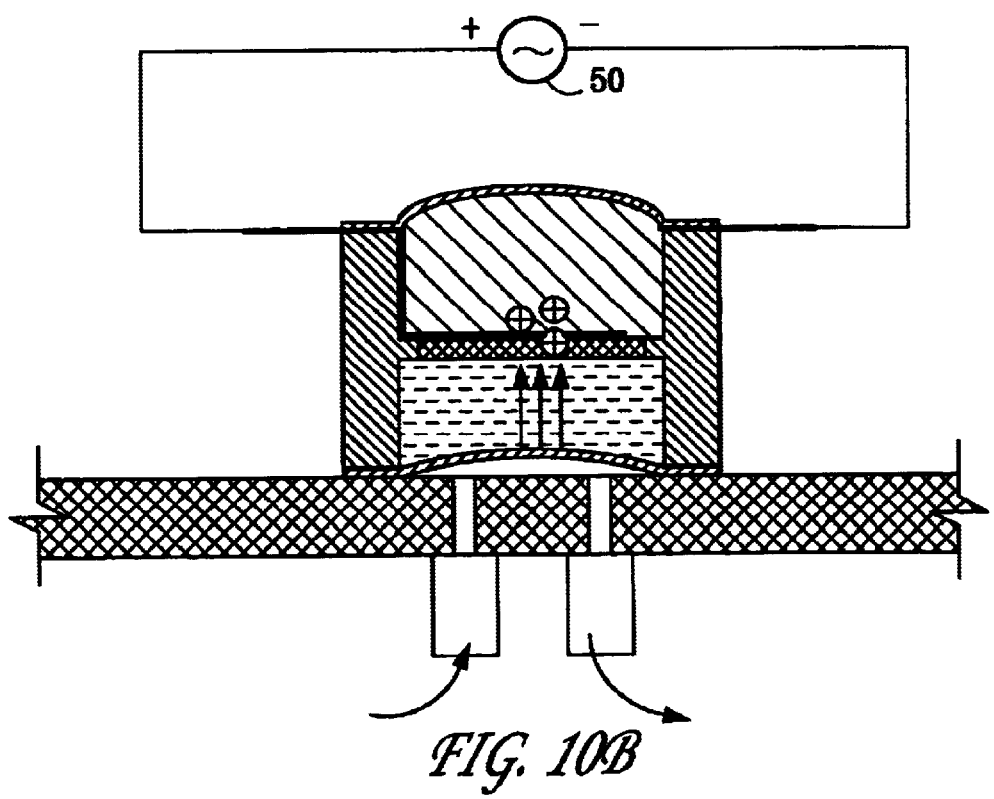
FIG. 10B illustrates the actuator assembly mounted onto a plenum in the first relationship and actuated by applying an electrical potential to the porous electrodes attached to the conductive gel plug so as to open a passage between the fluid channels.

As shown in FIG. 10B, assembly 40 can now be made to function as a valve assembly by again bonding assembly 40 along a region directly adjacent to surface 11, over plenum 45, wherein inlet and outlet channels 46 and 47 are situated. Alternatively, assembly 40 may be mechanically held against plenum 45 by a clamping means (not shown). Using a source 50 of electrical energy, typically a battery, a charged capacitor, or low voltage power supply, valve actuation is performed by applying a small voltage potential (about ±1V) across electrodes 15 of plug assembly 10. As shown in FIG. 10B, when an electrical potential is applied the polymer gel expands under the influence of migrating charge species (and their coordinating solvent molecules) diffusing into the gel body 12 from the reservoir of electrolyte 35 contained in the chamber opposite the gel body. The result is a net transfer of material from the electrolyte reservoir chamber into the gel chamber resulting in a net volume expansion of the gel body and a net volume contraction of the electrolyte reservoir. Because these chambers are sealed, this is outwardly manifested by an outward flexing of the disk 42 covering gel assembly 40, and an inward flexing of the disk 41 covering electrolyte 35. Disk 41, therefore, acts as a diaphragm which can be made to open or close orifices 46$a$ and 47$a$ allowing flowing between channels 46 and 47 by simple manipulation of the electrical potential applied across electrodes 11 attached to gel body 12.

Figure 10C:
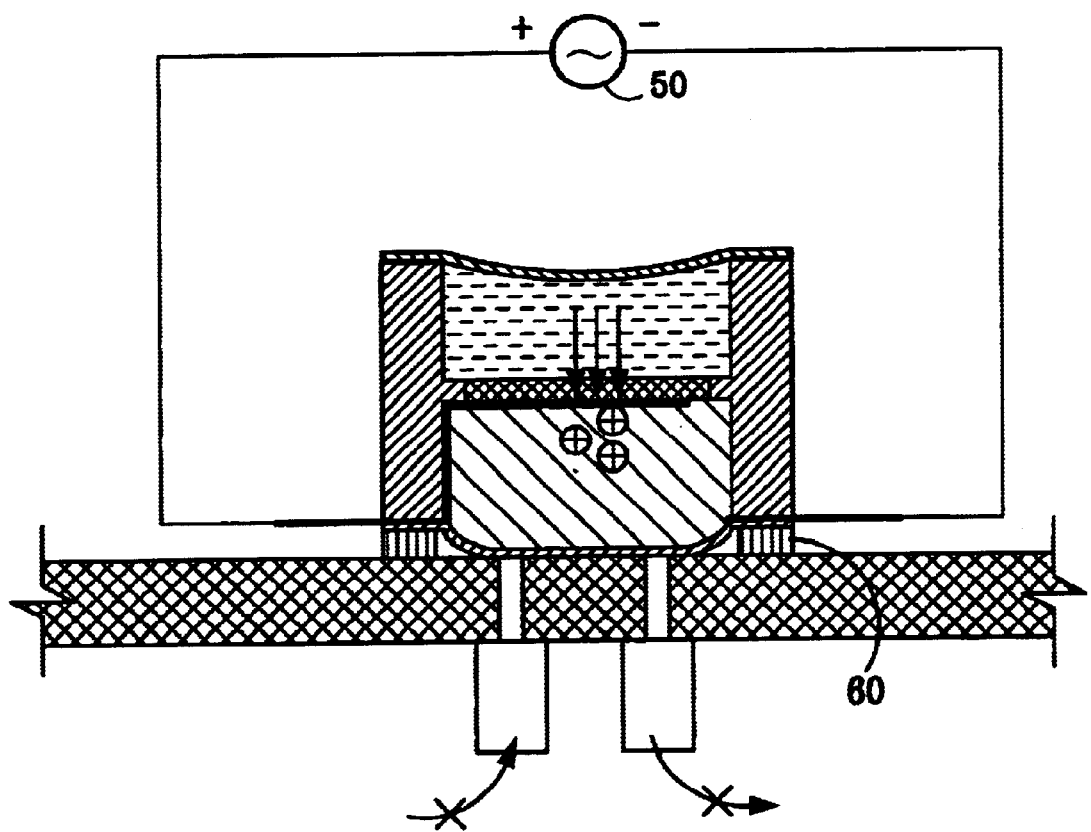
FIG. 10C illustrates the actuator assembly mounted onto a plenum in a second relationship and actuated so as to cover one or more fluid channels.

Finally, the technique can be further modified by placing the diaphragm on the inside of a valve housing, or raised above plenum 45 (as shown in FIG. 10C) by a ring or spaced assembly 60 such that diaphragm disk 41 over gel plug 12 can be made to expand against one or more orifices to block or regulate fluid flow, or contract to allow unrestricted flow through the valve. Such an assembly also could easily be made to operate as a rudimentary pump with the addition of a set of opposing check valves(flaps) over selected groups of fluid channels through plenum 45 so that as gel plug 12 changes state under the influence of the applied voltage, one valve is drawn open while the opposite valve is drawn shut. The pump would therefore operate by drawing a fluid into the space between the plenum, the spacer ring, and the gel plug, through one set of channels opening as the plug contracts and then disgorging the trapped fluid as the plug is expanded.

The foregoing list of examples is intended, therefore, to describe only a few of the possible embodiments. Other embodiments will be realized by those skilled in the art as each reads the description of the invention and the appended claims. The list of embodiments recited by the present invention, therefore, should not be construed to be exhaustive, nor should it limit the scope of the utility of this invention in any way.

What is claimed is:

1. An actuator assembly, comprising:
   a nonconductive housing having an exterior surface wall and first and second interior recessed portions, wherein said first and second interior portions are separated by a porous member;
   a plug assembly, comprising a conductive polymer plug having a top and a bottom surface, a first electrode disposed on and in contact with said top surface, and a second electrode disposed on and in contact with said bottom surface, wherein said conductive polymer plug is doped with an electrolyte solution comprising solvent coordinated anions, said plug assembly disposed in and filling said first recessed portion;
   a quantity of said electrolyte solution filling said second recessed portion;
   flexible means for covering and sealing said first and second recessed portions; and
   means for applying an electric potential across said top and bottom surface of said conductive polymer plug, wherein applying said electric potential to said first and second electrodes causes said solvent coordinated anions to migrate through said porous member and into said conductive polymer plug thereby causing said conductive polymer plug to increase in volume and cause said flexible means covering said conductive polymer plug to expand outward.

2. The actuator assembly of claim 1, wherein said conductive polymer plug is a gel.

3. The actuator assembly of claim 2, wherein said gel comprises polythiophene-based polymer gel cross-linked with 1,6-bis(2-thienyl)hexane.

4. The actuator assembly of claim 1, wherein said porous member is permeable to said solvent coordinated anions.

5. The actuator assembly of claim 4, wherein said porous member comprises a frit.

6. The actuator assembly of claim 5, wherein said frit comprises a material selected from the group consisting of a porous glass, a porous polymer, and a porous non-corroding metal.

7. The actuator assembly of claim 4, wherein said porous member comprises a material selected from the group consisting of glass, quartz, polyethylene polypropylene, and porous nickel.

8. The actuator assembly of claim 1, wherein said housing comprises a material selected from the group consisting of polymers, ceramics, glasses, silicon, and combinations thereof.

9. The actuator assembly of claim 1, wherein said polymers are selected from the group consisting of polytetrafluoroethylene, polymethylmethacrylate, polysulfones, polycarbonates, polyurethanes, polyimide resins, crystalline homopolymer acetal resins, and combinations thereof.

10. The actuator assembly of claim 1, wherein said glasses are selected from the group consisting of moldable or machinable glass, glass-ceramics, and combinations thereof.

11. The actuator assembly of claim 1, wherein said flexible means comprises a thin flexible layer of an elastomeric polymer, wherein said thin flexible layer covers only said first and second interior portions or completely surrounds and encapsulates said housing.

12. The actuator assembly of claim 1, wherein said flexible means comprises a thin flexible layer of a silicone conformal coating, a room temperature-vulcanizing polydimethylsiloxane, or a polyimide.

13. The actuator assembly of claim 1, wherein said means for applying an electric potential further comprises lead wires attached to said respective first and second electrodes.

14. The actuator assembly of claim 13, wherein said means for applying an electric potential further comprises a battery, a capacitor, or a low voltage power supply attached to said lead wires.

15. The actuator assembly of claim 1, further comprising a plenum having inlet and outlet orifices, said actuator assembly disposed on and sealed to said plenum, said actuator assembly engaging said plenum across an annulus, wherein said annulus large diameter coincides with said housing exterior surface wall.

16. A fluid pump, comprising:
    an actuator assembly, comprising:
      a nonconductive housing having an exterior surface wall and first and second interior recessed portions, wherein said first and second interior portions are separated by a porous member;
      a plug assembly, comprising a conductive polymer plug having a top and a bottom surface, a first electrode disposed on and in contact with said top surface, and a second electrode disposed on and in contact with said bottom surface, wherein said conductive polymer plug is doped with an electrolyte solution comprising solvent coordinated anions, said plug assembly disposed in and filling said first recessed portion;
      a quantity of said electrolyte solution filling said second recessed portion;
      flexible means for covering and sealing said first and second recessed portions; and
      means for applying an electric potential across said top and bottom surface of said conductive polymer plug, wherein applying said electric potential to said first and second electrodes causes said solvent coordinated anions to migrate through said porous member and into said conductive polymer plug thereby causing said conductive polymer plug to increase in volume and cause said flexible means covering said conductive polymer plug to expand outward; and
    a plenum having inlet and outlet orifices and a means for preventing fluid back-flow through said orifices, wherein said actuator assembly is disposed and sealed to said plenum such that said electrolyte reservoir lays over said orifices, said actuator assembly engaging said plenum across an annulus, wherein said annulus large diameter coincides with said housing exterior surface wall.

17. The fluid pump according to claim 16, wherein said means for preventing fluid back-flow comprises one-way check valves over or in said inlet and said outlet channels.

18. The fluid pump according to claim 16, wherein said check valves comprise hinged flaps.

* * * * *